Aug. 11, 1959 L. PETERS ET AL Plant Pat. 1,858
ROSE PLANT
Filed Dec. 4, 1958
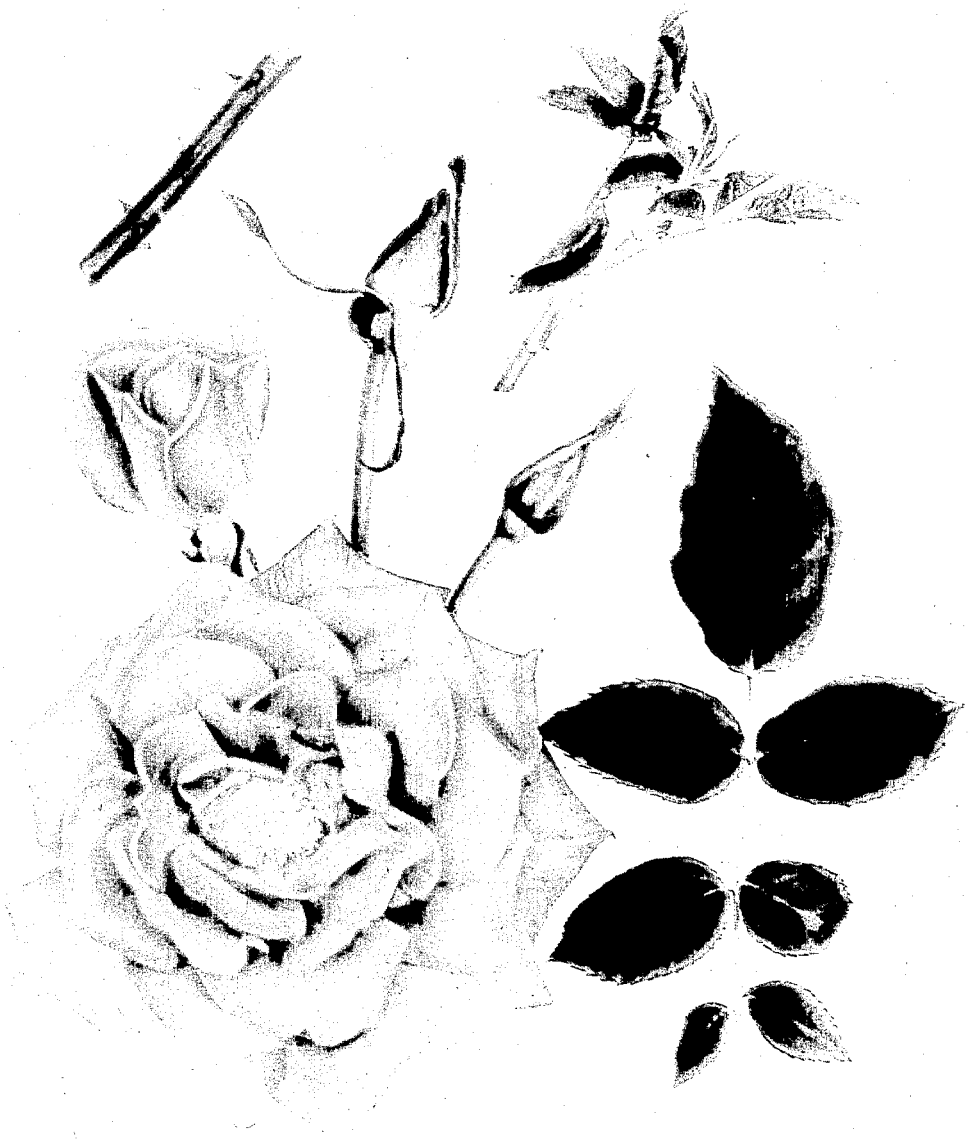
Inventors.
Lincoln Peters and
Norman Peters
By: Robbs & Robbs
Attorneys.

United States Patent Office

Plant Pat. 1,858
Patented Aug. 11, 1959

1,858

ROSE PLANT

Lincoln Peters and Norman Peters, Hempstead, N.Y., assignors to Geo. Peters & Sons, Inc., Hempstead, N.Y., a corporation of New York Application December 4, 1958, Serial No. 778,272

1 Claim. (Cl. 47—61)

The present invention relates to a new and distinct variety of rose plant of the hybrid tea class, which was discovered by us as a sport of the variety "Better Times" (Plant Patent No. 23).

This new sport was discovered by us in the benches of our greenhouse located on our property at Hempstead, Long Island, where we were growing the variety "Better Times" for cut flower use. During our cultivation of the "Better Times" plants in these greenhouses, our attention was attracted to one plant on which the blooms appeared to differ from the blooms normally borne by the "Better Times" variety. Upon closer examination of this plant, we found that it had sported, and we thereupon took steps to carefully preserve the sport, keep it under observation and to later asexually reproduce the same. These observations and asexual reproductions, as performed by own-root cuttings and also by budding, at Newark, New York, and Pleasanton, California, conclusively established important differences between the sport and the variety "Better Times," and that these differing characteristics were fixed and established, and capable of being transmitted through succeeding propagations.

Among the outstanding characteristics of the new variety, the following features contribute to the novelty and distinctiveness thereof, and represent a unique combination which is definitely different from that found in the parent variety, or in any other variety of which we are aware:

(1) Greater flower petalage, with the flowers averaging from 40 to 50 petals per bloom, as compared with 30 to 35 petals per bloom in the "Better Times" variety, according to the general average under normal growing conditions;

(2) An irregular habit of the sepals, characterized by one sepal being extra long, another being slightly shorter, and 3 sepals being of normal length;

(3) A deeper and more velvety appearance of the flower color, with the greater depth of color apparent on both surfaces of the petals, as compared with the flowers of "Better Times" which are much lighter in color on the reverse of the petals than on the opposite surface;

(4) Good persistence of the flower color, without appreciable change, from the bud stage to the fully open bloom;

(5) A distinctive Rose Red, lightly overcast with Amaranth Purple general color tonality of the blooms, presenting a very velvety appearance; and (6) A much heavier fragrance than that of "Better Times."

The accompanying drawing shows typical specimens of the vegetative growth and flowers of the new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Sport of "Better Times."

Classification:

*Botanic.*—Hybrid tea.

*Commercial.*—Hybrid tea.

Propagation: Holds its distinguishing characteristics through succeeding propagations by both cuttings and budding.

*Flower*

(Observations made from specimens grown in a greenhouse at Newark, New York, in the early afternoon in the latter part of August.)

Blooming habit: Recurrent—continuous.

Bud:

*Size.*—Large.

*Form.*—Pointed; is not affected by wet or hot weather.

*Color.*—When sepals first divide—Bordeaux, Plate 12. When petals begin to unfurl—Pomegranate Purple, Plate 12, lightly overcast with Carmine, Plate 1. When half-blown: inside of petals—Rose Red, Plate 12, heavily over-laid with Pomegranate Purple, Plate 12, giving a velvety appearance; reverse of petals—Tyrian Rose, Plate 12, lightly overcast with Amaranth Purple, Plate 12.

*Sepals.*—Slightly branched; hood above bud, with hood principally formed by one extra long sepal, one sepal slightly shorter, and 3 sepals of normal length; curl back when petals begin to unfurl. Color: inside—Turtle Green, Plate 32; outside—Chromium Green, Plate 32.

*Calyx.*—Color—Light Bice Green, Plate 17. Shape—funnel. Size—small. Aspect—smooth. Odor when rubbed—none.

*Peduncle.* — Length — long. Aspect — smooth. Strength—stiff; heavy. Color—Courge Green, Plate 17.

*Opening.*—Opens up well; is not affected by adverse weather conditions.

Bloom:

*Size.*—Large. Average size when fully expanded—from 4½ inches to 5 inches.

*Borne.*—Both singly and several together.

*Stems.*—Long; strong.

*Form (when first open).*—High-centered. Permanence—retains its form to the end, except that outer petals curl back slightly.

*Petalage.*—Double (full but open center). Number of petals under normal conditions—from 40 to 50.

*Color.*—Center of flower—Rose Red, Plate 12. Outer petals—Tyrian Rose, Plate 12, overlaid with Amaranth Purple, Plate 12. Base of petals (aiglet)—Clay Color, Plate 29. Inside of petals—Rose Red, Plate 12, overlaid with Amaranth Purple, Plate 12. Reverse of petals—Tyrian Rose, Plate 12. General tonality from a distance—Rose Red, Plate 12, overlaid with Amaranth Purple, Plate 12.

*Discoloration.*—General tonality at end of first day—Rose Red, Plate 12. Second day—Rose Red, Plate 12, overlaid with Amaranth Purple, Plate 12. Third day—Rose Red, Plate 12, lightly overcast with Amaranth Purple, Plate 12.

Petals:

*Texture.*—Leathery; is not affected by wet or hot weather.

*Appearance.*—Inside—velvety. Outside—shiny.

*Form.*—Oval.

*Arrangement.* — Imbricated (regularly arranged shingle-like).
*Petaloids in center.*—Few; large.
*Persistence.*—Drop off cleanly.
*Fragrance.*—Strong, and retained until the end. Nature—tea (average hybrid tea scent).
*Lasting quality.*—On the plant—long. As cut flower—very long.

*Genital organs*

Stamens, anthers: Medium size; many; regularly arranged around styles. Color—Capucine Yellow, Plate 3.
Stamens, filaments (threads): Medium length. Color—Tyrian Rose, Plate 12.
Pollen: Color—Light Buff, Plate 15.
Styles: Columnar; uneven length; medium length; thin.
Stigmas: Color—Light Ochraceous Salmon, Plate 15.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Normal.
*Color.*—New foliage: upper side—Madder Brown, Plate 13; under side—Van Dyke Red, Plate 13. Old foliage: upper side—Deep Dull Yellow-Green, Plate 32; under side—Malachite Green, Plate 32, lightly overcast with Deep Hellebore Red, Plate 38.
*Shape.*—Oval pointed.
*Texture.*—Upper side—leathery. Under side—smooth.

*Ribs and veins.*—Ordinary.
*Edge.*—Serrated (saw-toothed).
*Serration.*—Both double and single; small.
*Leaf stem.*—Color—Absinthe Green, Plate 31. Under side—smooth.
*Stipules.*—Long; smooth.
Wood:
*New wood.*—Color—Lettuce Green, Plate 5. Bark—smooth.
*Old wood.*—Color—Jade Green, Plate 31. Bark—smooth.
Thorns:
*Thorns.*—Quantity: on main stalks from base—few; on laterals from stalk—few. Form—narrow base; short; hooked downward. Color (when young)—Begonia Rose, Plate 1. Position—irregular.
*Prickles.*—Quantity: on main stalks—none; on laterals—none.
*Short needles.*—Quantity: on main stalks—none; on laterals—none.

We claim:

A new and distinct variety of rose plant of the hybrid tea class, substantially as herein shown and described, characterized particularly as to novelty by the unique combination of greater average flower petalage than that of its parent "Better Times" (Plant Patent No. 23), irregular length of the sepals, greater depth of color which is apparent on both sides of the flower petals, persistence of flower color without appreciable change from the bud stage to the fully open flower, a distinctive Rose Red, lightly overcast with Amaranth Purple, and velvety general color tonality of the blooms, and the relatively heavy fragrance of the flowers.

No references cited.